(12) United States Patent
Li et al.

(10) Patent No.: US 11,295,871 B2
(45) Date of Patent: Apr. 5, 2022

(54) COLLIMATOR ASSEMBLY AND RAY DETECTION APPARATUS

(71) Applicant: NUCTECH COMPANY LIMITED, Beijing (CN)

(72) Inventors: Hanping Li, Beijing (CN); Yuecheng Hu, Beijing (CN); Kun Zhao, Beijing (CN)

(73) Assignee: Nuctech Company Limited, Beijing (CN)

( * ) Notice: Subject to any disclaimer, the term of this patent is extended or adjusted under 35 U.S.C. 154(b) by 229 days.

(21) Appl. No.: 16/668,796

(22) Filed: Oct. 30, 2019

(65) Prior Publication Data

US 2020/0135356 A1 Apr. 30, 2020

(30) Foreign Application Priority Data

Oct. 31, 2018 (CN) .......................... 201811285591.6

(51) Int. Cl.
*G21K 1/02* (2006.01)
*A61B 6/06* (2006.01)

(52) U.S. Cl.
CPC ................ *G21K 1/025* (2013.01); *A61B 6/06* (2013.01); *G01N 2223/316* (2013.01); *G01N 2223/32* (2013.01)

(58) Field of Classification Search
CPC ........... A61B 6/06; A61B 6/40; A61B 6/4035; A61B 6/405; A61B 2560/00; A61B 2560/04; A61B 2560/06; G01T 1/29; G01T 1/2921; G01T 1/295; G21K 1/00; G21K 1/02; G21K 1/025; G21K 1/04; G21K 1/046; G21K 1/10; G21K 2201/00;
(Continued)

(56) References Cited

U.S. PATENT DOCUMENTS 3,849,649 A * 11/1974 Carey ...................... G21K 1/04
378/150
4,489,426 A 12/1984 Grass et al.
(Continued)

FOREIGN PATENT DOCUMENTS

| CN | 105708484 A | 6/2016 |
|---|---|---|
| EP | 1 026 698 A1 | 8/2000 |
| WO | 2015/176115 A1 | 11/2015 |

OTHER PUBLICATIONS

Great Britain Combined Search and Examination Report for corresponding Great Britain Application No. 1915869.0 dated Apr. 29, 2020, 7 pages.
(Continued)

*Primary Examiner* — Anastasia Midkiff
(74) *Attorney, Agent, or Firm* — Merchant & Gould P.C.

(57) ABSTRACT

The disclosure provides a collimator assembly, comprising at least at least two collimators configured to be moveable relative to each other such that the collimator assembly is switchable between at least two collimation modes; in respective collimation modes, the at least two collimators are superposed with each other in a thickness direction of the collimator assembly, such that the collimator assembly presents different combined patterns for collimating and shielding rays incident onto the collimator assembly and that the collimator assembly has corresponding ray shielding thickness for effectively shielding rays.

13 Claims, 9 Drawing Sheets

(58) Field of Classification Search
CPC ......... G01N 2223/30; G01N 2223/316; G01N 2223/32; G01N 2291/015; G02B 2207/129; G02B 21/0036; G02B 21/004; G02B 21/0044
See application file for complete search history.

(56) References Cited

U.S. PATENT DOCUMENTS

| | | | |
|---|---|---|---|
| 4,506,374 A | 3/1985 | Flynn | |
| 6,737,652 B2 * | 5/2004 | Lanza | G01T 1/295 250/237 R |
| 7,623,614 B2 * | 11/2009 | Shefsky | G01N 23/02 378/2 |
| 8,243,353 B1 * | 8/2012 | Gutin | G03H 1/2286 359/21 |
| 9,414,800 B2 * | 8/2016 | Takagi | A61B 6/08 |
| 2017/0186507 A1 | 6/2017 | Kang et al. | |

OTHER PUBLICATIONS

Preliminary Search Report for French Patent Application No. 1 912 246 dated Apr. 30, 2021, 18 pages.
Examination Report for United Kingdom Patent Application No. GB1915869.0 dated May 11, 2021, 2 pages.

* cited by examiner

COLLIMATOR ASSEMBLY AND RAY DETECTION APPARATUS

CROSS-REFERENCE TO RELATED APPLICATION

This application claims the priority benefit of the Chinese Patent Application No. 201811285591.6 filed on Oct. 31, 2018 in the China National Intellectual Property Administration, the whole disclosure of which is incorporated herein by reference.

TECHNICAL FIELD

Embodiments of the present disclosure generally relate to the field of ray detection technologies, and particularly, to a collimator assembly having adjustable collimation modes and/or thickness, and a ray detection apparatus having the collimator assembly.

DESCRIPTION OF THE RELATED ART

A ray detection apparatus such as a gamma camera can detect a presence of radioactivity in a monitored area and a spatial distribution of intensity of radioactivity in the monitored area, and accurately determine the type of radionuclide so as to quickly and accurately determine a position of a radioactive material in the monitored area. The ray detection apparatus, such as a gamma camera, is mainly used in monitoring of a nuclear power plant, supervision of a radioactive source, customs and the like. Collimator is one of core components of the ray detection apparatus, and its main function is to collimate and shield incident rays. The rays, after being collimated and shielded, form a corresponding projection image on a detector. The quality of the projection image has an important influence on an imaging quality of a system. Therefore, selection of collimation modes of the collimator and setting of geometric parameters of the collimator will directly affect the imaging effect of the system.

After installation of the collimator of the existing ray detection apparatus, the mode and size of the collimator are fixed accordingly. When the ray energy and the application scene change, the collimator having a single mode and a single thickness is not adaptive to the change, resulting in failing of the system to achieve a desired imaging effect. Although the thickness and mode may be changed by disassembling and replacing the collimator, a variety of collimators need to be carried for replacement in use, and the replacement time is longer, which affects work efficiency.

SUMMARY

The present disclosed has been made to at least partly solve or alleviate at least one of the above mentioned and other disadvantages or problems in prior art.

In an aspect of the present disclosure, an embodiment provides a collimator assembly, comprising at least a first collimator and a second collimator, the first collimator and the second collimator being configured to be moveable relative to each other such that the collimator assembly is switchable at least between a first collimation mode and a second collimation mode, in the first collimation mode, the first collimator and the second collimator are superposed with each other in a thickness direction of the collimator assembly, such that the collimator assembly has a first combined pattern for collimating and shielding rays incident onto the collimator assembly and such that a portion of the collimator assembly for shielding the rays has a first ray shielding thickness;

in the second collimation mode, the first collimator and the second collimator are superposed with each other in the thickness direction of the collimator assembly, such that the collimator assembly has a second combined pattern for collimating and shielding rays incident onto the collimator assembly and such that another portion of the collimator assembly for shielding the rays has a first ray shielding thickness; and the first combined pattern is different from the second combined pattern, and the first ray shielding thickness is different from the second ray shielding thickness.

In some embodiments, the first collimator includes a first pattern for collimating and shielding rays incident onto the first collimator; and the second collimator includes a second pattern for collimating and shielding rays incident onto the second collimator, and different combinations of the second pattern and the first pattern in the first collimation mode and the second collimation mode defines the first combined pattern and the second combined pattern respectively.

In some embodiments, the second pattern is different from the first pattern.

In some embodiments, the first pattern and the second pattern are complementary to each other.

In some embodiments, the first pattern and the second pattern are configured such that in one of the first collimation mode and the second collimation mode, one of the first pattern and the second pattern is at least partly embedded into the other of the first pattern and the second pattern.

In some embodiments, one of the first combined pattern and the second combined pattern is different from each of the first pattern and the second pattern.

In some embodiments, at least one of the first pattern and the second pattern includes a MURA coded pattern.

In some embodiments, one of the first combined pattern and the second combined pattern includes a MURA coded pattern, and the other of the first combined pattern and the second combined pattern includes a single-pinhole pattern or a multi-pinhole pattern.

In some embodiments, a part of the first pattern for shielding the rays has a first thickness, while a part of the second pattern for shielding the rays has a second thickness; one of the first ray shielding thickness and the second ray shielding thickness is equal to a sum of the first thickness and the second thickness; and the other of the first ray shielding thickness and the second ray shielding thickness is equal to, at a first position of the collimator assembly, the first thickness, and is equal to, at a second, other position of the collimator assembly, the second thickness.

In some embodiments, the first pattern of the first collimator comprises: a plurality of first ray transmission regions configured to allow rays incident onto the first collimator to pass through the first collimator; and a plurality of first ray shielding regions delimiting the plurality of first ray transmission regions and configured to block the rays incident onto the first collimator from passing through the first collimator; and the second pattern of the second collimator comprises: a plurality of second ray transmission regions configured to allow rays incident onto the second collimator to pass through the second collimator; and a plurality of second ray shielding regions arranged to at least surround the plurality of second ray transmission regions and configured to block the rays incident onto the second collimator from passing through the second collimator.

In some embodiments, the plurality of second ray shielding regions are configured to be at least partly embeddable into the plurality of second ray transmission regions in one of the first collimation mode and the second collimation mode.

In some embodiments, the first collimator comprises a first plate defining the first pattern, the plurality of first ray transmission regions include a plurality of opening holes extending through the first plate, and the plurality of first ray shielding regions includes parts of the first plate made of a first ray shielding material; and/or, the second collimator comprises a second plate and a mesh patterned structure, the second plate is made of a ray transmission material, the mesh patterned structure comprises a plurality of protrusions extending from one surface of the second plate toward the first collimator and a plurality of mesh holes delimited by the plurality of protrusions, the plurality of protrusions are made of a second ray shielding material, and the mesh patterned structure is disposed on a surface of the second plate so as to define, together with the second plate, the second pattern, such that the plurality of protrusions form the plurality of second ray shielding regions, and parts of the second plate corresponding to the plurality of mesh holes define the plurality of second ray transmission regions.

In some embodiments, the first collimator and the second collimator are configured to be moveable with respect to each other in the thickness direction and be rotatable with respect to each other about an axis extending in the thickness direction, such that the collimator assembly is switchable between the first collimation mode and the second collimation mode.

In some embodiments, the second collimator is configured to abut against a surface of the first collimator in the second collimation mode, and is rotatable with respect to the first collimator about the axis by an angle and is moveable toward the first collimator in the thickness direction so as to be at least partly embedded into the first collimator, thereby switching from the second collimation mode to the first collimation mode.

In another aspect of the present disclosure, an embodiment provides a ray detection apparatus, comprising: the collimator assembly described in any of embodiments of the present disclosure, the collimator assembly being configured for collimating and shielding rays from a ray source; and a detector configured to receive the collimated rays from the collimator assembly and to generate a signal indicative of the received rays.

Other features and advantages of the present disclosure will become more apparent by describing in detail exemplary embodiments thereof with reference to the accompanying drawings, which may help comprehensive understanding of the present disclosure.

BRIEF DESCRIPTION OF THE DRAWINGS

Features and advantages of the present disclosure can be understood more clearly with reference to the accompanying drawings, which are illustrative and should not be construed as being limitative to the disclosure. In the drawings.

DETAINED DESCRIPTION OF EXEMPLARY EMBODIMENTS

Figure 1:
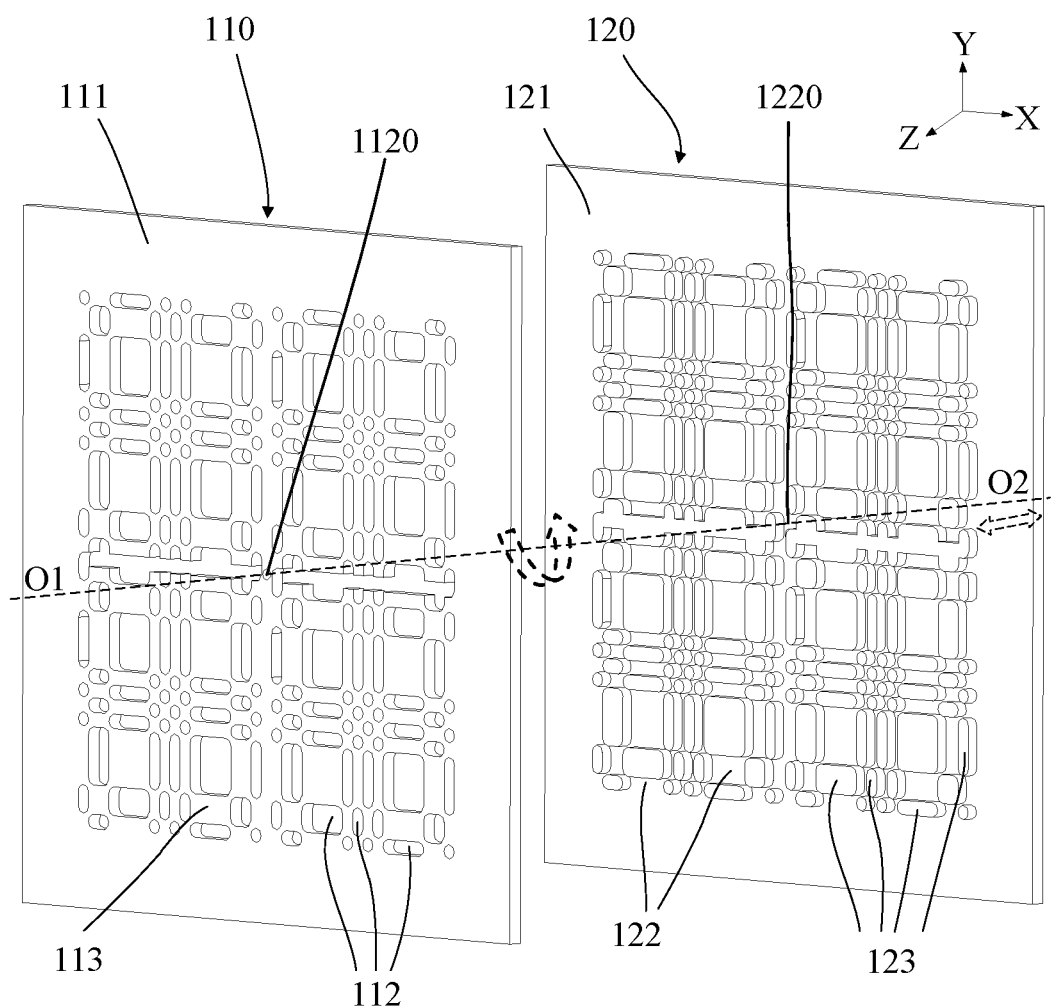
FIG. 1 is an exploded perspective view schematically showing an arrangement of a collimator assembly, in a first collimation mode, according to an exemplary embodiment of the present disclosure.

Technical solutions of the present disclosure will be further described in detail in combination with exemplary embodiments with reference to the attached drawings. Obviously, the embodiments described are only parts, not all, of embodiments of the present disclosure. Based on the embodiments described in the present disclosure, all of other embodiments, which made by those skilled in the art without involving in creative works, also fall within scopes of the present disclosure.

Further, in the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to a general concept of the present disclosure, a collimator assembly comprises at least two collimators, a collimation mode (including, for example, a pattern for collimating and shielding rays, a ray shielding thickness or effective ray shielding thickness, or the like) of the collimator assembly for rays can be changed or switched through relative movement (e.g., rotation and/or linear movement), thereby it is possible to realize applications in various occasions, where detection conditions such as the ray energies or application scenes are changed, without replacing the collimator(s).

Exemplarily, the collimator assembly comprises two collimators, and the two collimator are configured to be moveable relative to each other, such that the collimator assembly is switchable between at least two collimation modes; in respective collimation modes, the two collimator are superposed with each other in a thickness direction of the collimator assembly, such that the collimator assembly can present or have different combined patterns for collimating and shielding rays incident onto the collimator assembly, and such that the collimator assembly can present or have corresponding ray shielding thicknesses for effectively shielding the rays. For example, in the first collimation mode, the two collimator are superposed with each other in a thickness direction of the collimator assembly, such that the collimator assembly presents or has a first combined pattern for collimating and shielding rays incident onto the collimator assembly and such that a portion of the collimator assembly for shielding the rays has a first ray shielding thickness; in the second collimation mode, the two collimators are superposed with each other in the thickness direction of the collimator assembly, such that the collimator assembly presents or has a second combined pattern for collimating and shielding rays incident onto the collimator assembly, and such that another (e.g., different) portion of the collimator assembly for shielding the rays has a second ray shielding thickness. The combined pattern of the collimator assembly is provided by a combination of patterns of the two collimators themselves for collimating and shielding rays, and the first combined pattern is different from the second combined pattern; an effective ray shielding thickness of the collimator assembly is provided by a combination of thicknesses of portions of the two collimators themselves for shielding rays, and the first ray shielding thickness is different from the second ray shielding thickness. Therefore, switching of collimation modes characterized by at least the combined pattern and/or ray shielding thickness for collimating and shielding rays can be achieved.

It is noted that in this text, the pattern of the collimator or the combined pattern of the collimator assembly refers to an orthographic projection formed by radiation rays or other light rays incident onto and passing through the collimator or collimator assembly. The ray shielding thickness of the collimator or collimator assembly refers to a thickness or size of a portion of the collimator or collimator assembly that can effectively shield or block the incident rays. Depending on requirements for ray collimating and shielding in the application scene, the collimation modes of the collimator assembly can be switched through a relative movement between the collimators, such that the collimator assembly can have or present corresponding or different combined patterns and/or ray shielding thicknesses in different applications; for different application scenes, the collimator assembly may have the same or different patterns and/or ray shielding thicknesses at its various positions.

In embodiments of the present disclosure, the collimator assembly may include at least two collimators that can move relative to each other to change the collimation mode, and the combined patterns presented in different collimation modes may include a MURA coded pattern, a pinhole pattern or the like. In the text, for convenience of explanation, it will be only taken as an example that the collimator assembly includes two collimators and has two collimation modes. Of course, according to the description herein, those skilled in the art can easily conceive an arrangement of a collimator assembly including more collimators and switching among more collimation modes.

Figure 6:
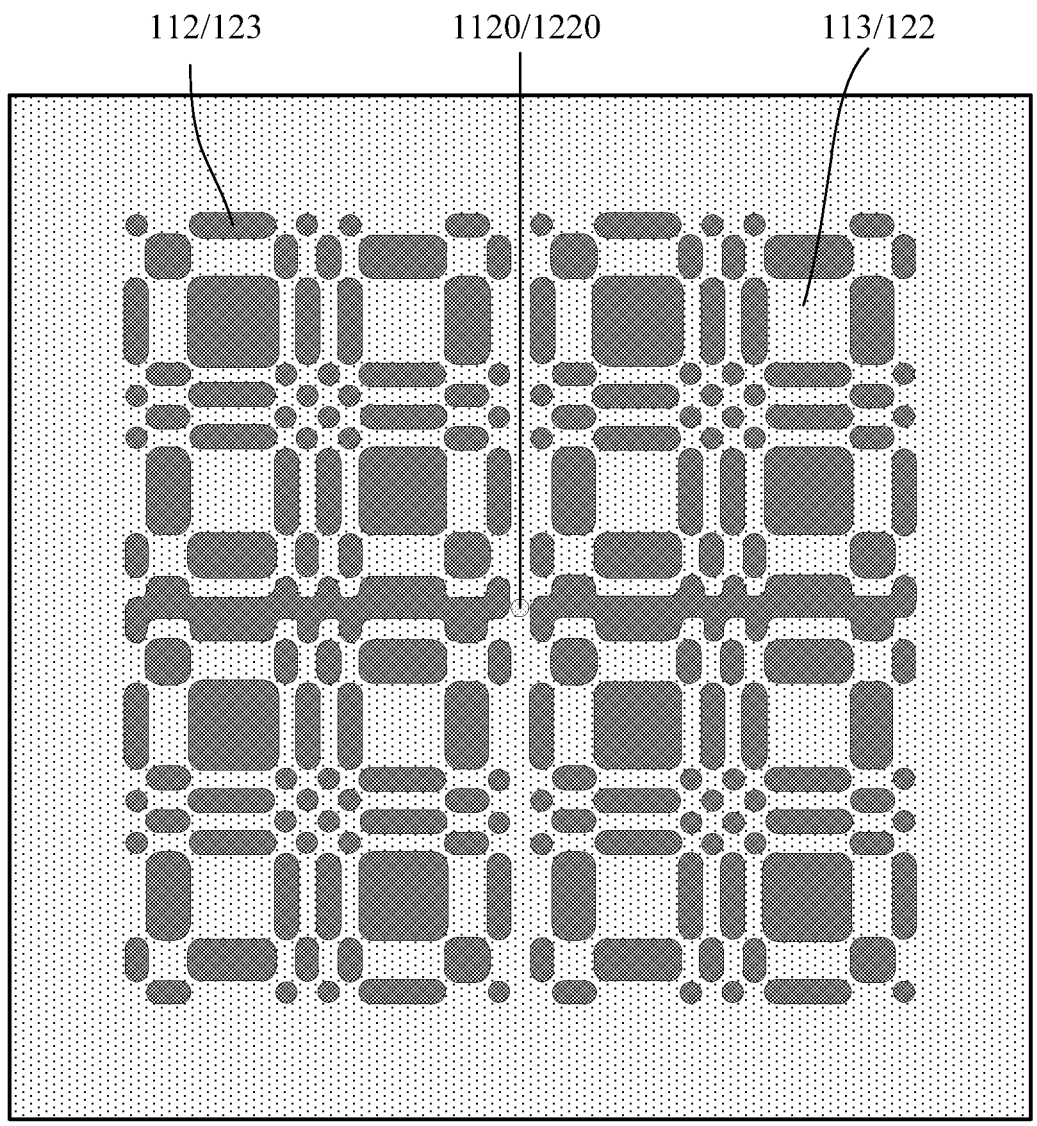
FIG. 6 is a front view schematically showing a projection pattern of a collimator assembly, in a first collimation mode, according to an exemplary embodiment of the present disclosure.
Figure 7:
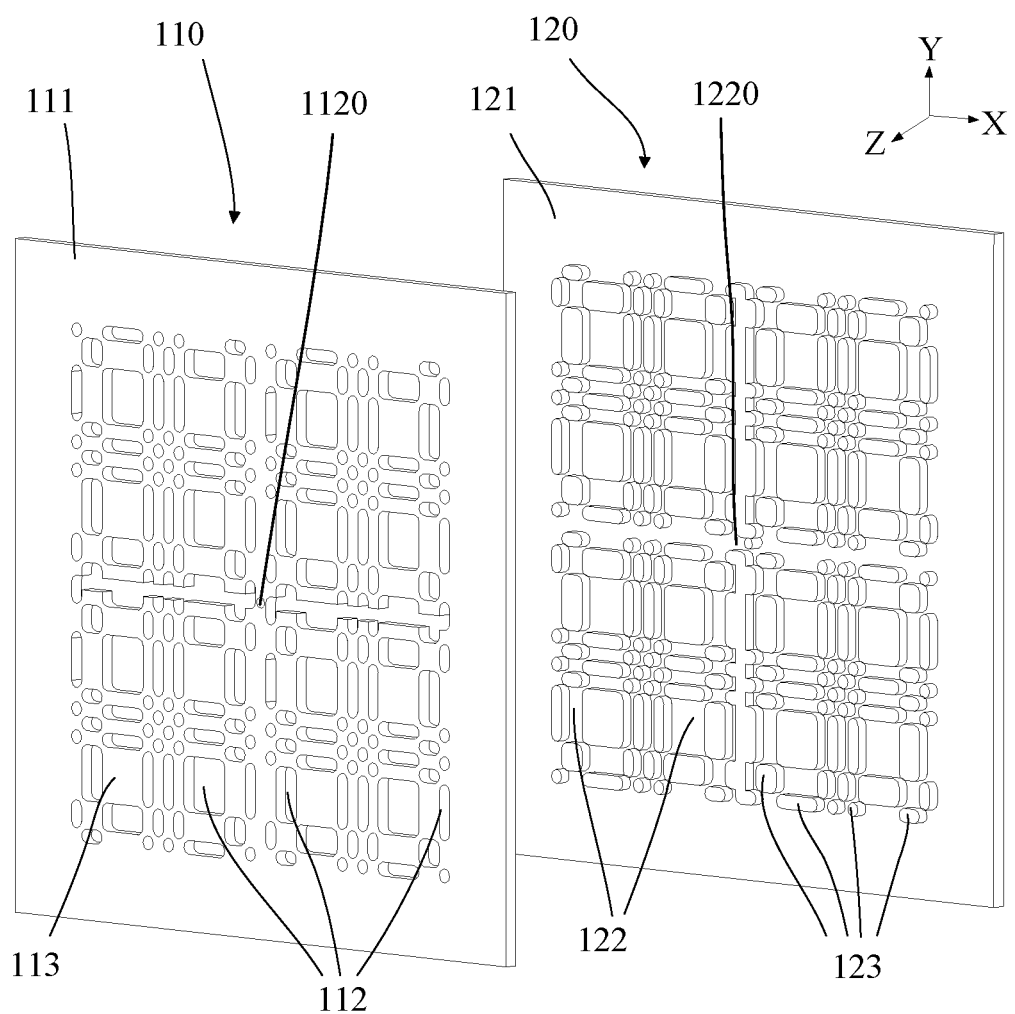
FIG. 7 is an exploded perspective view schematically showing an arrangement of a collimator assembly, in a second collimation mode, according to an exemplary embodiment of the present disclosure.
Figure 8:
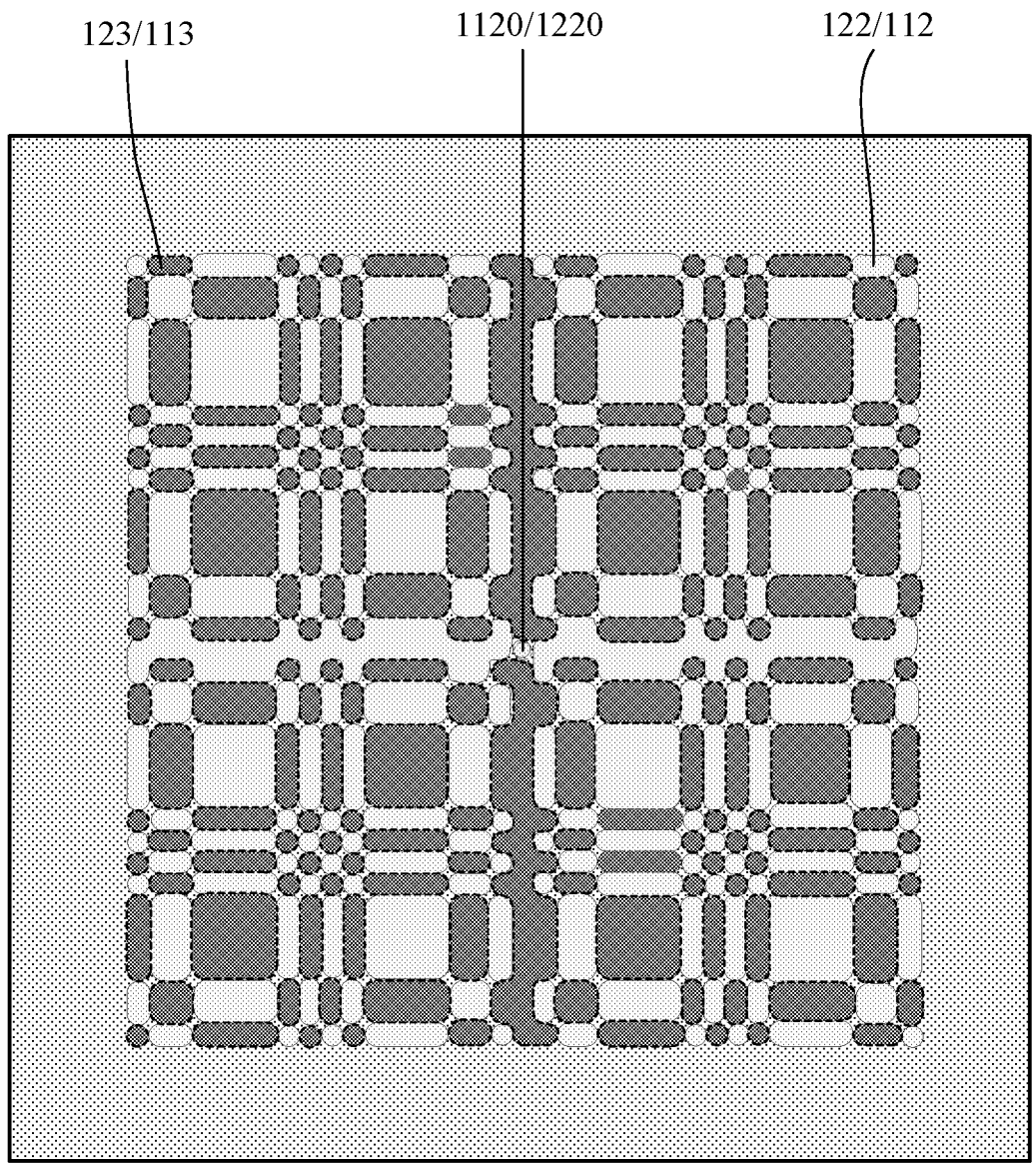
FIG. 8 is a front view schematically showing a projection pattern of a collimator assembly, in a second collimation mode, according to an exemplary embodiment of the present disclosure.

FIG. 1 is a exploded perspective view schematically showing a structure or arrangement of a collimator assembly, in a first collimation mod, according to an exemplary embodiment of the present disclosure, FIG. 7 is a exploded perspective view schematically showing a structure or arrangement of a collimator assembly, in a second collimation mod, according to an exemplary embodiment of the present disclosure, and FIGS. 6 and 8 schematically show projection patterns of the collimator assembly, in the first collimation mode and the second collimation mode respectively, according to exemplary embodiments of the present disclosure. As illustrated, a collimator assembly comprises a first collimator 110 and a second collimator 120, the first collimator and the second collimator configured to be moveable relative to each other, such that the collimator assembly is switchable at least between the first collimation mode and the second collimation mode. Exemplarily, by means of a relative movement (including a rotation movement, a linear movement, or the like) between the collimators, corresponding combined patterns and/or combined or effective ray shielding thicknesses can be achieved in respective collimation modes of the collimator assembly by a combination of patterns of and/or a combination of thicknesses of the first collimator 110 and the second collimator 120 themselves for collimating and shielding rays.

For example, in the first collimation mode shown in FIG. 1, the first collimator 110 and the second collimator 120 are superposed with each other in the thickness direction (e.g., a z-axis direction in the figure) of the collimator assembly, such that the collimator assembly presents or has a first combined pattern for collimating and shielding rays incident onto the collimator assembly, as shown in FIG. 6, and such that a portion of the collimator assembly for shielding the rays has a first ray shielding thickness; in the second collimation mode shown in FIG. 7, the first collimator 110 and the second collimator 120 are superposed with each other in the thickness direction (e.g., a z-axis direction in the figure) of the collimator assembly, such that the collimator assembly presents or has a second combined pattern for collimating and shielding rays incident onto the collimator assembly, as shown in FIG. 8, and such that a (for example, another or different) portion of the collimator assembly for shielding the rays has a second ray shielding thickness. In the illustrated embodiments, the first combined pattern is different from second combined pattern, and the first ray shielding thickness is different from the second ray shielding thickness.

Figure 2:
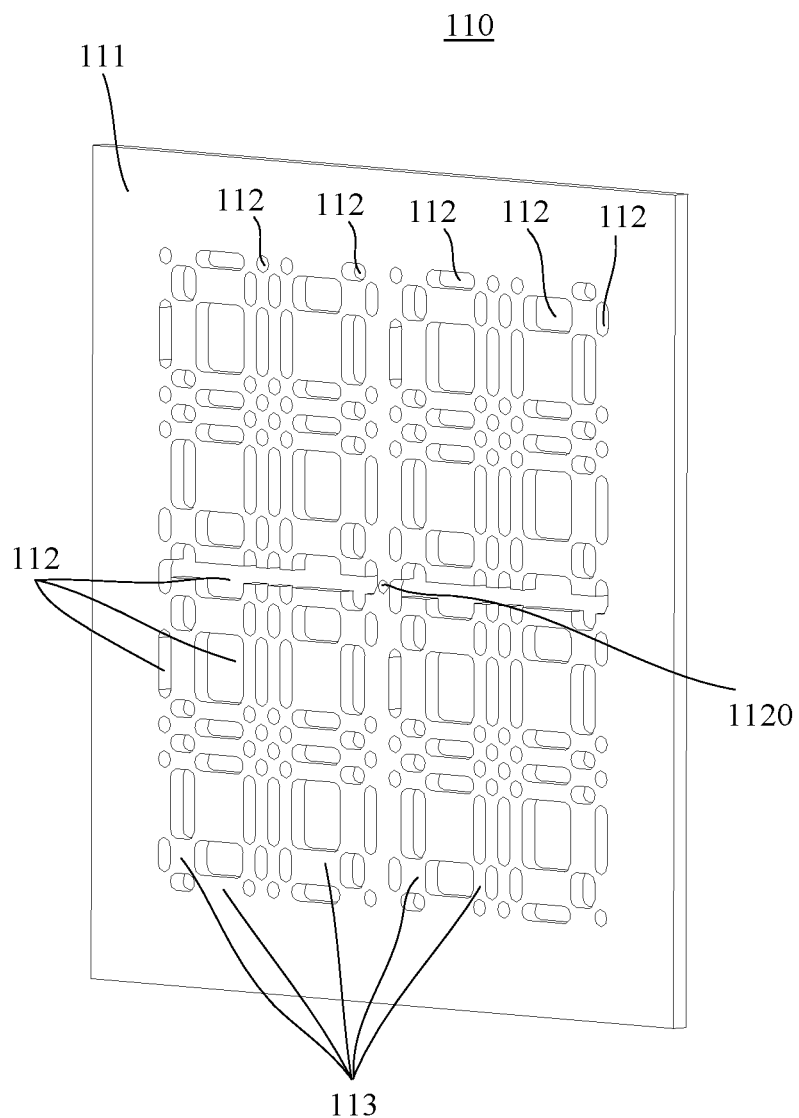
FIG. 2 is a perspective view schematically showing a structure of a first collimator of a collimator assembly according to an exemplary embodiment of the present disclosure.
Figure 3:
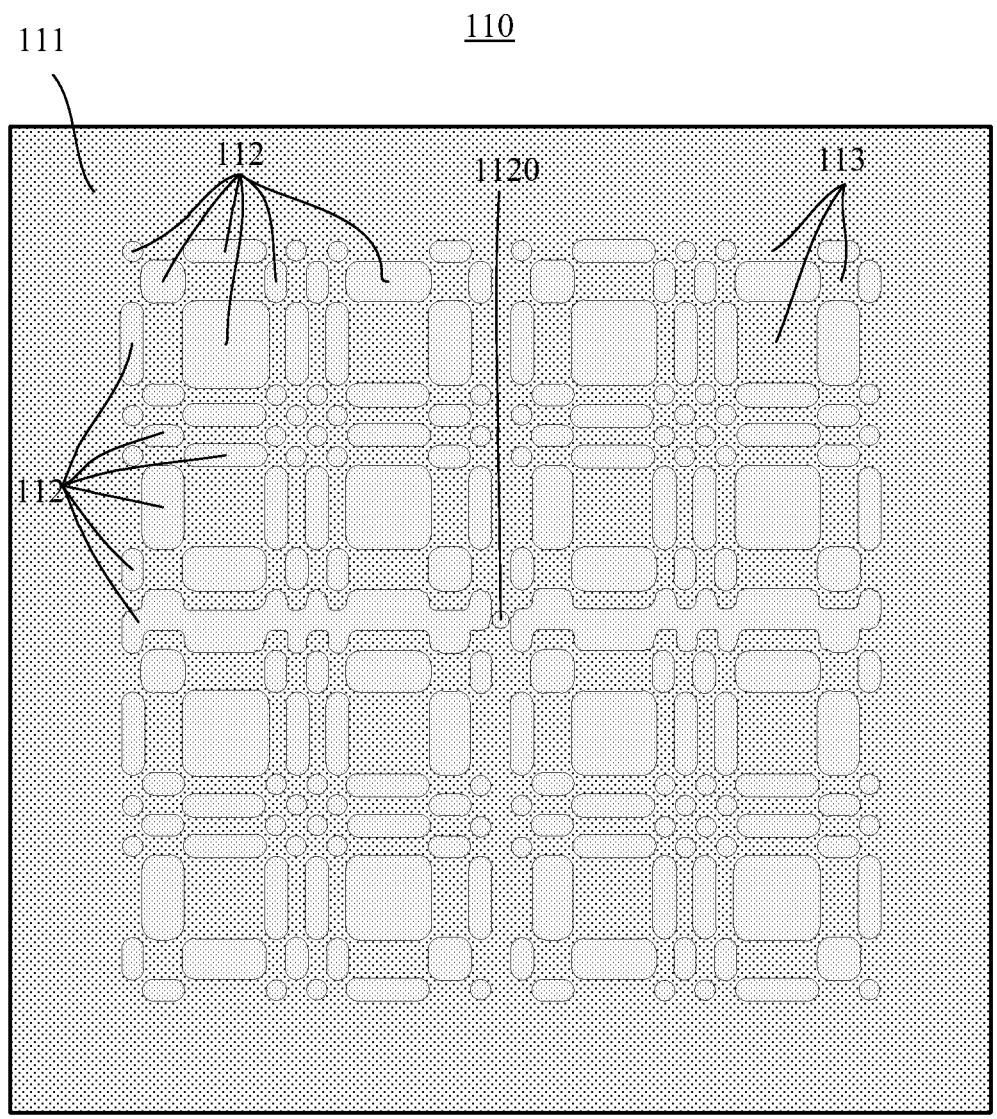
FIG. 3 is a front view schematically showing a pattern of a first collimator according to an exemplary embodiment of the present disclosure.
Figure 4:
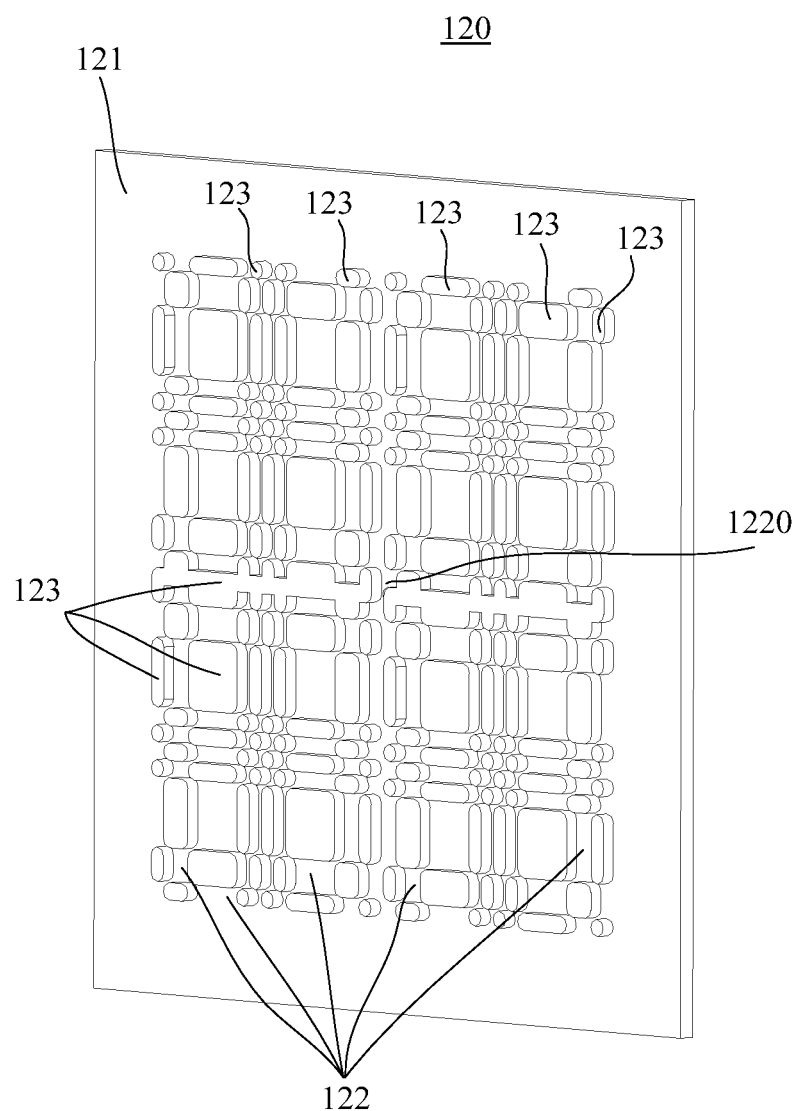
FIG. 4 is a perspective view schematically showing a structure of a second collimator of a collimator assembly according to an exemplary embodiment of the present disclosure.
Figure 5:
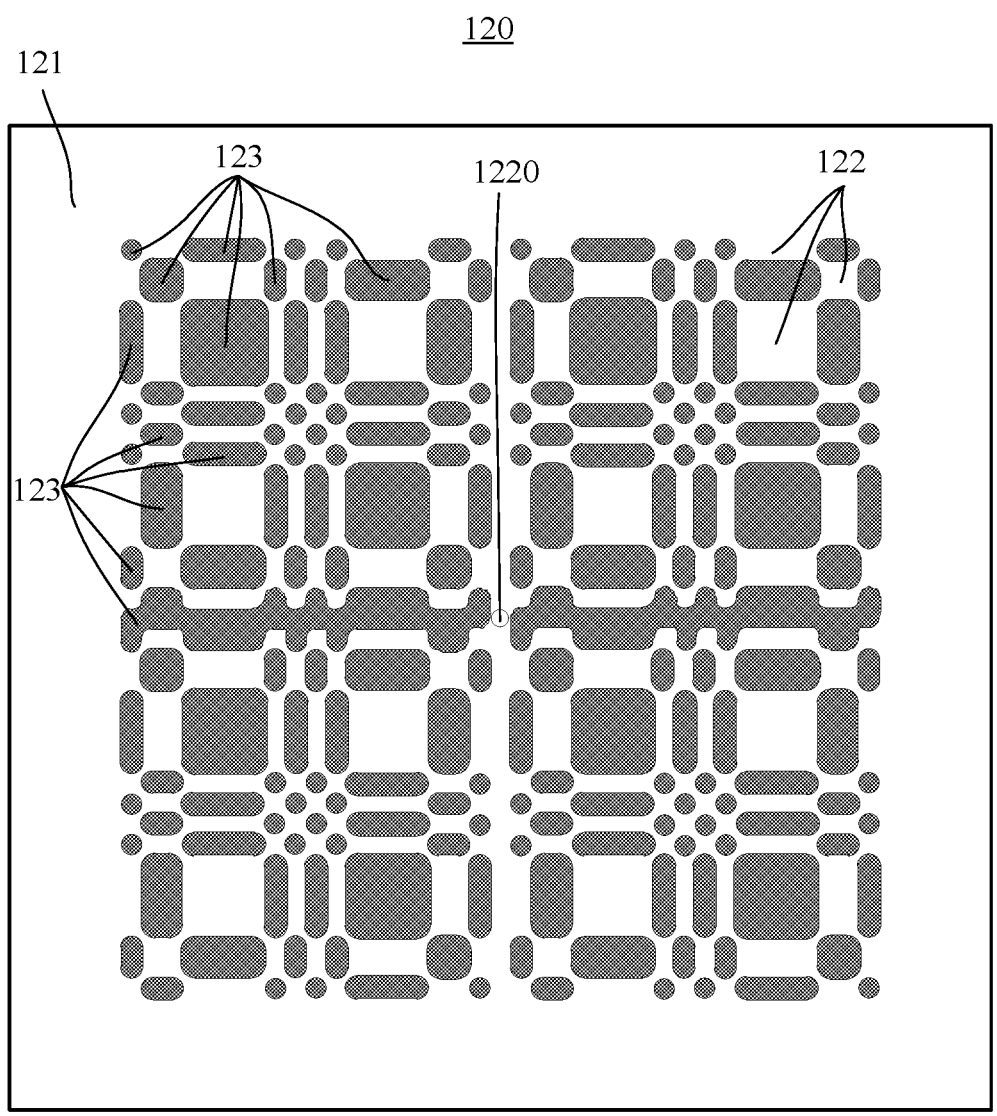
FIG. 5 is a front view schematically showing a pattern of a second collimator according to an exemplary embodiment of the present disclosure.

FIGS. 2-5 schematically show structures and patterns of the first collimator and the second collimator of the collimator assembly according to exemplary embodiments of the present disclosure. As shown in FIGS. 2 and 3, the first collimator 110 has or defines a first pattern for collimating and shielding rays incident onto the first collimator; as shown in FIGS. 4 and 5, the second collimator 120 has or defines a second pattern for collimating and shielding rays incident onto the second collimator. Different combinations of the second pattern and the first pattern achieved in the first collimation mode and the second collimation mode define the first combined pattern and the second combined pattern of the collimator assembly respectively, as shown in FIGS. 6 and 8.

In the illustrated embodiments, the first pattern of the first collimator 110 is different from the second pattern of the second collimator 120. For example, as shown in FIGS. 3 and 5, the first pattern and second pattern are completely or at least partially complementary to each other, such that in the first collimation mode shown in FIG. 1, one of the first pattern and the second pattern is at least partly embedded into the other of the first pattern and the second pattern, for example, protrusion structures of the second pattern are at least partly embedded into opening holes of the first pattern, thereby forming the first combined pattern of the collimator assembly, as shown in FIG. 5.

In some examples, at least one of the first pattern and the second pattern includes a MURA coded pattern, for example 19×19 MURA coded pattern, 11×11 MURA coded pattern, 7×7 MURA coded pattern or the like, or may also include a pinhole pattern. As shown in FIGS. 2-5, the first pattern and the second pattern are each MURA coded patterns, which are different from each other, for example, are patterns complementary to each other. Illustratively, a MURA coded pattern comprises opening part having openings and a solid material part surrounding the opening, and after being rotated by an angle (e.g., 90 degrees), the rotated MURA coded pattern is complementary to the original MURA coded pattern at locations except the center location thereof, that is, the opening part of a MURA coded pattern obtained through rotation (that is, the rotated MURA coded pattern) is located at the same position as the solid material part of the original MURA coded pattern before rotation and has substantially the same or similar section shape (herein, the section shape refers to for example a shape of a cross section perpendicular to the thickness direction of the collimator or collimator assembly) as the solid material part of the original MURA coded pattern, while the solid material part of the MURA coded pattern obtained through rotation is located at the same position as the opening part of the original MURA coded pattern before rotation and has substantially the same or similar section shape as the opening part of the original MURA coded pattern. In some embodiments, the first pattern and the second pattern are different MURA coded patterns, and are complementary to each other, that is, the MURA coded pattern as the second pattern is, after being rotated by an angle (e.g., 90 degrees), complementary to the MURA coded pattern as the first pattern.

Exemplarily, in the first collimation mode shown in FIGS. 1 and 6, the first collimator 110 and the second collimator 120 are superposed with each other in the thickness direction, such that portions of the second pattern for shielding or blocking rays from passing therethrough and portions (e.g., openings or opening holes) of the first pattern for allowing rays to pass therethrough are corresponding in position to each other, for example, their orthographic projections overlap with each other; meanwhile, another portions of the second pattern for allowing rays to pass or be transmitted therethrough and another portions of the first pattern for shielding or blocking rays from passing therethrough are also corresponding in position to each other, for example, their orthographic projections overlap with each other, thereby achieving the patterns being complementary to each other. In some examples, the portions of the second pattern for shielding or blocking rays from passing therethrough have substantially the same or similar section shape as the portions of the first pattern for allowing rays to pass therethrough, such that the portions of the second pattern for shielding or blocking rays from passing therethrough may be completely or partially embedded into the portions of the first pattern for allowing rays to pass therethrough to achieve a combination of the first and second patterns, thereby forming the first combined pattern of the collimator assembly, as shown in FIG. 6.

In the embodiments shown in FIGS. 1-3, the first patterns of the first collimator 110 comprises a plurality of first ray transmission regions and a plurality of first ray shielding regions 113, the first ray transmission regions are configured to allow rays incident onto the first collimator 110 to pass through the first collimator 110, and the first ray shielding regions 113 delimit the first ray transmission regions and are configured to shield or block rays incident onto the first collimator 110 from passing through the first collimator.

As shown in FIGS. 1-3, the first collimator 110 comprises a first plate 111 defining the first pattern, for example, a MURA coded plate, the first plate 111 comprises or is provided with a plurality of opening holes or openings extending through the first plate, for example comprises a first central hole 1120 and holes 112 located around the central hole. These opening holes or openings may include circular holes, strip-shaped holes, square holes, elliptic holes or other polygonal holes, and may be arranged regularly or irregularly and spaced apart from one another. These opening holes or openings form the first ray transmission regions of the first collimator 110, and portions of the first plate 111 surrounding or delimiting these opening holes or openings are made of a ray shielding or blocking material so as to form the first ray shielding regions 113 of the first collimator 110, thereby forming a desired pattern, such as a MURA coded pattern or pinhole pattern. Thickness(es) of the portions of the first plate 111 surrounding or delimiting these opening holes or openings define(s) or equal(s) to the ray shielding thickness of the first collimator 110, that is, the first thickness.

Exemplarily, the first collimator may be manufactured by patterning, for example, by forming holes, in a ray shielding or blocking material plate, such as a plate of high blocking ability material (e.g., tungsten copper alloy). In an example, the first collimator may be formed by forming an opening hole at a center position of a conventional MURA coded plate collimator.

It will be understood that the arrangement of the ray transmission regions (e.g., opening holes, openings, through holes) is not limited to those illustrated in the figures, and may be set as required; further, the ray transmission regions of the first collimator are not limited to the form of opening holes, openings or through holes, and in other embodiments, the ray transmission regions or portions of the first collimator may also include recesses or blind holes which allow passing of rays therethrough, or may be made of a material which allows passing of rays therethrough.

In the embodiments shown in FIGS. 1 and 4-5, the second pattern of the second collimator 120 comprises a plurality of second ray transmission regions and a plurality of second ray shielding regions, the second ray transmission regions are configured to allow rays incident onto the second collimator 120 to pass through the second collimator 120, and the second ray shielding regions delimit the second ray transmission regions and are configured to shield or block rays incident onto the second collimator 120 from passing through the second collimator.

As shown in FIGS. 1 and 4-5, the second collimator 120 comprises a second plate 121 and a mesh patterned structure, the second plate 121 is made of a ray transmission material, the mesh patterned structure may form or define a pattern (e.g., a MURA coded pattern or a pinhole pattern) matching (e.g., complementary to) the pattern of the first collimator 110, and the mesh patterned structure is arranged or formed in a surface of the second plate 121, so as to define, together with the second plate, the second pattern of the second collimator. The mesh patterned structure may a plurality of protrusions 123 extending from a surface of the second plate 121 towards the first collimator 110 and a plurality of mesh holes 122, 1220 delimited by the plurality of protrusions, including a central hole 1220 defined by adjacent protrusions 123 and a plurality of mesh holes 122 disposed and distributed around the central hole 1220.

The protrusions 123 is made of a ray shielding material so as to form or define the second ray shielding regions of the second collimator 120, while portions of the second plate 121 corresponding to the mesh holes 122, 1220 define the plurality of second ray transmission regions. The protrusions may have a circular section shape, a strip section shape, a square section shape, an elliptic section shape or other polygonal section shape, and may be arranged regularly or irregularly and spaced apart from one another, as required in practice. The mesh holes 122, 1220 or the second ray transmission regions may be disposed around the protrusions 123.

If the second plate 121 is made of a ray transmission material, a height of the protrusion 123 or a distance of the protrusion 123 extending from the surface of second plate, defines or equals to a ray shielding thickness of the second collimator 120, that is, the second thickness. In other embodiments, the second plate may be formed of a ray transmission material at positions corresponding to the mesh holes, or may be formed with openings, opening holes, through holes or blind holes, as long as it is ensured that the second plate allows rays to pass therethrough at the positions corresponding to the mesh holes, and may be made of a ray shielding material or a ray partial-transmission material at positions corresponding to the protrusions. In this case, the ray shielding thickness of the second collimator 120 is equal to a sum of the height of the protrusion and an effective ray shielding thickness of a portion of the second plate at a position corresponding to the protrusion.

Exemplarily, when manufacturing the second collimator, the second plate may be provided firstly, then a mesh-patterned structure formed by a ray shielding material (for example, a plate of high-blocking ability material, such as tungsten-copper alloy) may be provided (e.g., adhered) or formed on the second plate; the second plate may be made of a ray transmission material (such as plastic); or, the second plate may be formed by a ray transmission material or formed with openings, opening holes, through holes or blind holes at positions corresponding to the mesh holes, and may be formed by a ray shielding material or a ray partial-transmission material at positions corresponding to the protrusions. Thereby, a combination of the second plate and the mesh patterned structure provides a desired projection pattern, such as a MURA coded pattern, for shielding and collimating incident rays. Of course, in other embodiments, the second collimator may not require the second plate, and a ray collimation and shielding pattern is only provided by, for example, an integrated mesh patterned structure; for example the respective protrusions of the mesh patterned structure are connected to each other, for example by connection parts made of a ray transmission material, thereby forming an integral structure.

In the following, switching between different collimation modes of the collimator assembly provided by embodiments of the present disclosure will be described with reference to the accompanying figures.

In embodiments of the present disclosure, the first and second collimators of the collimator assembly are configured to be moveable relative to each other (e.g., towards or away from each other) in the thickness direction of the collimator assembly (as indicated by a two-way dashed arrow shown in FIG. 1) and to be rotatable about an axis extending in the thickness direction relative to each other, such that the collimator assembly is switchable between the first collimation mode and the second collimation mode.

In the first collimation mode, as shown in FIG. 1, the first collimator 110 and the second collimator 120 are superposed with each other in the thickness direction (e.g., Z direction shown in the Figure) of the collimator assembly, and the second collimator 120 abut against a surface of the first collimator 110, such that portions of the pattern of the second collimator 120 are embedded into the first collimator 110, thereby forming the first combined pattern of the collimator assembly, as shown in FIG. 6.

Exemplarily, in the first collimation mode, the second ray shielding region of the second collimator 120 is at least partially embedded or inserted into the corresponding first ray transmission region of the first collimator 110, for example, the protrusion 123 is completely or partially embedded or inserted into the corresponding hole 112, and the protrusion 123 has the same or similar section shape as the corresponding hole 112; similarly, the second ray transmission region of the second collimator 120 is aligned with the corresponding first ray shielding region of the first collimator 110 in the thickness direction. In other examples, the second ray shielding region of the second collimator needs not to be embedded into the corresponding first ray transmission region of the first collimator, and rather, is located close to and aligned with the corresponding first ray transmission region of the first collimator in the thickness direction. Thus, a combination of the patterns of the first and second collimators forms a first combined pattern of the collimator assembly; at this time, the second ray shielding region of the second collimator is aligned with the corresponding first ray transmission region of the first collimator in the thickness direction, the second ray transmission region of the second collimator is aligned with the corresponding first ray shielding region of the first collimator in the thickness direction, and the central hole 1220 of the second collimator is aligned with the central hole 1120 of the first collimator in the thickness direction.

In the illustrated embodiments, the first combined pattern is a pinhole pattern, such as a single-pinhole pattern, as shown in FIG. 6; in other embodiments, a plurality of ray transmission regions of the second collimator are aligned with a plurality of ray transmission regions (e.g., holes) of the first collimator in the thickness direction such that the formed first combined pattern may also be a multi-pinhole pattern. The first combined pattern may be different from the pattern of the first collimator and/or the pattern of the second collimator.

A portion, which is configured for shielding rays, of the first pattern of the first collimator has a first thickness, and a portion, which is configured for shielding rays, of the second pattern of the second collimator has a second thickness; in a case where the first collimator comprises a first plate provided with holes (e.g., a MURA coded plate), the first thickness is equal to a thickness of the first plate; in a case where the second collimator comprises a transmissive second plate and a patterned structure provided on the second plate, the second thickness is equal to a thickness or height of the patterned structure or the protrusion of the patterned structure or is equal to a distance of the protrusion extending from the second plate, and obviously, the second thickness for shielding rays is less than a sum of the thickness of the patterned structure and the thickness of the second plate.

In the first collimation mode, the first ray shielding thickness of the collimator assembly includes the first thickness and the second thickness, that is, the first ray shielding thickness is equal to the first thickness (e.g., the ray shielding thickness of the first plate) at a position of the collimator assembly corresponding to or aligning with the ray shielding region of the first collimator or the ray transmission region of the second collimator, and is equal to the second thickness (e.g., the height of the protrusion for ray shielding) at another position of the collimator assembly corresponding to or aligning with the ray transmission region of the first collimator or the ray shielding region of the second collimator. Apparently, a first combined thickness of the collimator assembly in the first collimation mode is less than a sum of the first thickness and the second thickness for ray shielding. Further, in the first collimation mode, since the first collimator and the second collimator may be arranged in such a way that they are at least partially embedded into each other, the formed collimator assembly has a smaller overall profile.

In some embodiments, the second ray shielding region of the second collimator has a section shape which is the same as or similar to that of the corresponding first ray transmission region of the first collimator, the second ray transmission region of the second collimator has a section shape which is the same as or similar to that of the corresponding first ray shielding region of the first collimator, and the central hole of the second collimator has a section shape which is the same as or similar to that of the central hole of the first collimator. In the first collimation mode, when the ray shielding regions and the corresponding ray transmission regions of the first collimator and the second collimator are aligned with each other in the thickness direction, the formed first combined pattern is a single-pinhole pattern if the dimension of the second ray shielding regions is larger than or equal to the dimension of the corresponding first ray transmission region, and may include a multi-pinhole pattern if the dimension of the second ray shielding region is less than the dimension of the corresponding first ray transmission region.

In other embodiments, it is not necessary for the ray shielding regions and the corresponding ray transmission regions of the first collimator and the second collimator to be exactly aligned with each other in the first collimation mode; for example, when the second collimator is superposed on the first collimator in such a way that it is not embedded into the first collimator, the second ray shielding region of the second collimator is offset from the corresponding first ray transmission region of the first collimator in a direction (first direction) perpendicular to the thickness direction so that a ray transmission hole is formed, the second ray transmission region of the second collimator is offset from the corresponding first ray shielding region of the first collimator in a direction (which may be the same as or different from the first direction) perpendicular to the thickness direction so that another ray transmission hole is formed, and the central hole of the second collimator is offset from the central hole of the first collimator in a direction (which may also be the same as or different from the first direction) perpendicular to the thickness direction so that a further ray transmission hole is formed, thereby forming a pattern having a plurality of ray transmission holes.

In some embodiments, the second collimator 120 is rotatable relative to the first collimator 110 by an angle (e.g., 90 degrees) about an axis O1-O2 extending in the thickness direction, as indicated by a curved dashed arrow shown in FIG. 1, such that the collimator assembly is switchable from the first collimation mode to the second collimation mode. During this switching, if the second collimator 120 is partially embedded into the first collimator 110 in the first collimation mode, the second collimator 120 may be moved away from the first collimator 110 in the thickness direction (e.g., Z direction) so as to be disassembled or separated from the first collimator, and then is rotated by a corresponding angle with respect to the first collimator; if the second collimator 120 is arranged in such a way that it is located close to the first collimator 110 but is not embedded into the first collimator 110 in the first collimation mode, the second collimator 120 may be directly rotated relative to the first collimator.

Through such relative movement between the second collimator and the first collimator, the second ray shielding regions of the second collimator may be brought into being aligned with the corresponding first ray shielding regions of the first collimator in the thickness direction, and the second ray transmission regions of the second collimator may be brought into being aligned with the corresponding first ray shielding regions of the first collimator in the thickness direction, thereby a combination of the patterns of the first collimator and the second collimator forms the second combined pattern of the collimator assembly, achieving the second collimation mode of the collimator assembly. In the second collimation mode, the central hole 1220 of the second collimator may be also aligned with the central hole 1120 of the second collimator in the thickness direction. Further, in the second collimation mode, the second collimator may abut against the first collimator, or may be spaced apart from the first collimator at a distance.

In some embodiments, the section shape of the second ray shielding region of the second collimator is the same as that of the corresponding first ray shielding region of the first collimator, the section shape of the second ray transmission region of the second collimator is the same as that of the corresponding first ray transmission region of the first collimator, and the section shape of the central hole second collimator is the same as that of the central hole of the first collimator. In the second collimation mode, the corresponding ray shielding regions and ray transmission regions of the first collimator and the second collimator may be aligned with each other in the thickness direction or slightly offset from each other in a direction perpendicular to the thickness direction. As can be seen from FIGS. 3 and 8, the second combined pattern presented by the collimator assembly in the second collimation mode is the same as or similar to the first pattern of the first collimator, and is complementary to the second pattern of the second collimator.

In the second collimation mode, if the corresponding ray shielding regions and ray transmission regions of the first collimator and the second collimator are aligned with each other in the thickness direction, the second ray shielding thickness of the collimator assembly is equal to a sum of the first thickness, for ray shielding, of the first collimator and the second thickness, for ray shielding, of the second collimator; if the corresponding ray shielding regions and ray transmission regions of the first collimator and the second collimator are slightly offset from each other in a direction perpendicular to the thickness direction, the second ray shielding thickness of the collimator assembly is: when measured at some positions (e.g., positions where portions of the second ray shielding regions are aligned with portions of the first ray shielding regions), equal to a sum of the first thickness, for ray shielding, of the first collimator and second thickness, for ray shielding, of the second collimator; when measured at other positions (e.g., positions where portions of the second ray shielding regions are aligned with portions of the first ray transmission regions), equal to the second thickness, for ray shielding, of the second collimator; when measured at some positions (e.g., positions where portions of the second ray transmission regions are aligned with portions of the first ray shielding regions), equal to the first thickness, for ray shielding, of the first collimator. Thereby, a pattern and a ray shielding thickness, which are different from those in the first collimation mode, may be achieved in the second collimation mode, in order to meet different application requirements.

Figure 9:
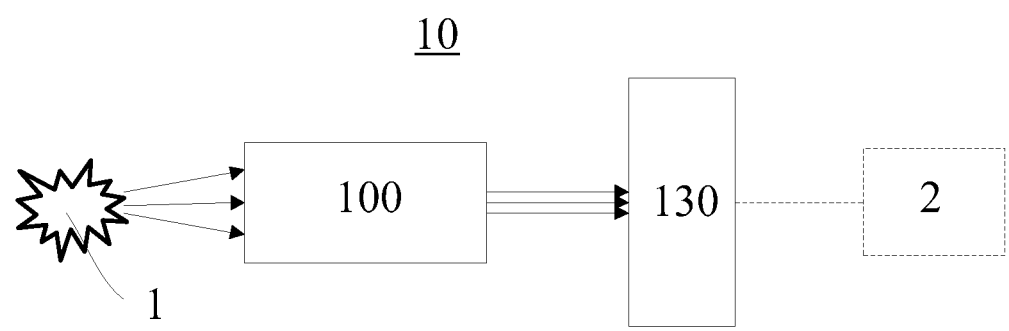
FIG. 9 is a block diagram schematically showing an arrangement of a ray detection apparatus according to an exemplary embodiment of the present disclosure.

In some embodiments of the present disclosure, there is further provided a ray detection apparatus, for example a gamma (γ) ray camera. As shown in FIG. 9, a ray detection apparatus 10 comprises a collimator assembly 100 and a detector 130, the collimator assembly 100 may include the collimator assembly described in any of the embodiments of the present disclosure, and is configured for collimating and shielding rays (e.g., γ rays) from a ray source 1, and the detector 130 is configured to receive the collimated rays from the collimator assembly 100 and to generate a signal indicative of the received rays. For example, the signal may be indicative of a presence or absence of radioactivity in a monitored area, a spatial distribution of intensity of radioactivity in the monitored area, the type of radionuclide, or the like. Based on the signal, a ray projection image may be formed or displayed at the ray detection apparatus (for example, on the detector) or on a remote monitor 2, enabling ray detection.

Although some of embodiments according to a general concept of the present disclosure have been illustrated and explained, the skilled person in the art will understand that these embodiments may be modified without departing principles and spirits of the present disclosure. The scope of the present disclosure will be defined by the appended claims and equivalents thereof.

What is claimed is:

1. A collimator assembly, comprising at least a first collimator and a second collimator, the first collimator and the second collimator being configured to be moveable relative to each other such that the collimator assembly is switchable at least between a first collimation mode and a second collimation mode,
   in the first collimation mode, the first collimator and the second collimator are superposed with each other in a thickness direction of the collimator assembly, such that the collimator assembly has a first combined pattern for collimating and shielding rays incident onto the collimator assembly and such that a portion of the collimator assembly for shielding the rays has a first ray shielding thickness, wherein the rays comprise one or more of gamma rays, x-rays, and incident light rays,
   in the second collimation mode, the first collimator and the second collimator are superposed with each other in the thickness direction of the collimator assembly, such that the collimator assembly has a second combined pattern for collimating and shielding rays incident onto the collimator assembly and such that another portion of the collimator assembly for shielding the rays has a second ray shielding thickness, and
   the first combined pattern is different from the second combined pattern, and the first ray shielding thickness is different from the second ray shielding thickness,
   wherein the first collimator comprises a first pattern for collimating and shielding rays incident onto the first collimator; and
   the second collimator comprises a second pattern for collimating and shielding rays incident onto the second collimator, and different combinations of the second pattern and the first pattern in the first collimation mode and the second collimation mode defines the first combined pattern and the second combined pattern respectively,
   wherein the first pattern and the second pattern are configured such that in one of the first collimation mode and the second collimation mode, one of the first pattern and the second pattern is at least partly embedded into the other of the first pattern and the second pattern.

2. The collimator assembly according to claim 1, wherein the second pattern is different from the first pattern.

3. The collimator assembly according to claim 1, wherein the first pattern and the second pattern are complementary to each other.

4. The collimator assembly according to claim 1, wherein one of the first combined pattern and the second combined pattern is different from each of the first pattern and the second pattern.

5. The collimator assembly according to claim 1, wherein at least one of the first pattern and the second pattern includes a MURA coded pattern.

6. The collimator assembly according to claim 1, wherein, one of the first combined pattern and the second combined pattern comprises a MURA coded pattern, and the other of the first combined pattern and the second combined pattern comprises a single-pinhole pattern or a multi-pinhole pattern.

7. The collimator assembly according to claim 1, wherein,
   a part of the first pattern for shielding the rays has a first thickness, while a part of the second pattern for shielding the rays has a second thickness,
   one of the first ray shielding thickness and the second ray shielding thickness is equal to a sum of the first thickness and the second thickness, and
   the other of the first ray shielding thickness and the second ray shielding thickness is equal to, at a first position of the collimator assembly, the first thickness, and is equal to, at a second position of the collimator assembly, the second thickness.

8. The collimator assembly according to claim 1, wherein, the first pattern of the first collimator comprises:
   a plurality of first ray transmission regions configured to allow rays incident onto the first collimator to pass through the first collimator; and
   a plurality of first ray shielding regions delimiting the plurality of first ray transmission regions and configured to block the rays incident onto the first collimator from passing through the first collimator; and
   the second pattern of the second collimator comprises:
   a plurality of second ray transmission regions configured to allow rays incident onto the second collimator to pass through the second collimator; and
   a plurality of second ray shielding regions arranged to at least surround the plurality of second ray transmission regions and configured to block the rays incident onto the second collimator from passing through the second collimator.

9. The collimator assembly according to claim 8, wherein the plurality of second ray shielding regions are configured to be at least partly embeddable into the plurality of second ray transmission regions, in one of the first collimation mode and the second collimation mode.

10. The collimator assembly according to claim 8, wherein,
   the first collimator comprises a first plate defining the first pattern, the plurality of first ray transmission regions comprise a plurality of opening holes extending through the first plate, and the plurality of first ray shielding regions comprise parts of the first plate made of a first ray shielding material; and
   the second collimator comprises a second plate and a mesh patterned structure, the second plate is made of a ray transmission material, the mesh patterned structure comprises a plurality of protrusions extending from one surface of the second plate toward the first collimator and a plurality of mesh holes delimited by the plurality of protrusions, the plurality of protrusions are made of a second ray shielding material, and the mesh patterned structure is disposed on a surface of the second plate so as to define, together with the second plate, the second pattern, such that the plurality of protrusions form the plurality of second ray shielding regions, and parts of the second plate corresponding to the plurality of mesh holes define the plurality of second ray transmission regions.

11. The collimator assembly according to claim 1, wherein,
the first collimator and the second collimator are configured to be moveable with respect to each other in the thickness direction and be rotatable with respect to each other about an axis extending in the thickness direction, such that the collimator assembly is switchable between the first collimation mode and the second collimation mode.

12. The collimator assembly according to claim 11, wherein,
the second collimator is configured to abut against a surface of the first collimator in the second collimation mode, and is rotatable with respect to the first collimator about the axis by an angle and is moveable toward the first collimator in the thickness direction so as to be at least partly embedded into the first collimator, thereby switching from the second collimation mode to the first collimation mode.

13. A ray detection apparatus, comprising:
the collimator assembly of claim 1, the collimator assembly being configured for collimating and shielding rays from a ray source; and
a detector configured to receive the collimated rays from the collimator assembly and to generate a signal indicative of the received rays.

* * * * *